(12) United States Patent
Bucci et al.

(10) Patent No.: US 9,138,264 B2
(45) Date of Patent: Sep. 22, 2015

(54) LAMINOPLASTY ROD SYSTEM

(75) Inventors: Kara A. Bucci, Chicago, IL (US); Daniel Predick, Chicago, IL (US); Howard S. An, Glenview, IL (US)

(73) Assignee: Life Spine, Inc., Huntley, IL (US)

( * ) Notice: Subject to any disclaimer, the term of this patent is extended or adjusted under 35 U.S.C. 154(b) by 671 days.

(21) Appl. No.: 12/917,666

(22) Filed: Nov. 2, 2010

(65) Prior Publication Data
US 2011/0106168 A1 May 5, 2011

Related U.S. Application Data

(60) Provisional application No. 61/257,312, filed on Nov. 2, 2009.

(51) Int. Cl.
A61B 17/70 (2006.01)

(52) U.S. Cl.
CPC ......... *A61B 17/7071* (2013.01); *A61B 17/7032* (2013.01); *A61B 17/7005* (2013.01); *A61B 17/7007* (2013.01); *A61B 17/7011* (2013.01); *A61B 17/7067* (2013.01)

(58) Field of Classification Search
CPC ........... A61B 17/7041; A61B 17/7035; A61B 17/7011
USPC .......................... 606/250, 254, 261–266, 278
See application file for complete search history.

(56) References Cited

U.S. PATENT DOCUMENTS

| | | | | |
|---|---|---|---|---|
| 5,254,118 A * | 10/1993 | Mirkovic | | 606/264 |
| 5,468,241 A * | 11/1995 | Metz-Stavenhagen et al. | | 606/319 |
| 5,498,262 A * | 3/1996 | Bryan | | 606/252 |
| 5,591,165 A * | 1/1997 | Jackson | | 606/264 |
| 5,593,407 A * | 1/1997 | Reis | | 606/261 |
| 5,683,391 A * | 11/1997 | Boyd | | 606/264 |
| 5,741,255 A * | 4/1998 | Krag et al. | | 606/264 |
| 5,947,965 A * | 9/1999 | Bryan | | 606/86 A |
| 5,951,553 A * | 9/1999 | Betz et al. | | 606/279 |
| 6,296,643 B1 * | 10/2001 | Hopf et al. | | 606/263 |
| 6,355,038 B1 * | 3/2002 | Pisharodi | | 606/300 |
| 6,648,885 B1 * | 11/2003 | Friesem | | 606/278 |
| 6,669,697 B1 * | 12/2003 | Pisharodi | | 606/264 |
| 7,591,836 B2 * | 9/2009 | Dick et al. | | 606/246 |
| 7,815,666 B2 * | 10/2010 | Baynham et al. | | 606/280 |
| 8,002,809 B2 * | 8/2011 | Baynham | | 606/282 |
| 8,177,814 B2 * | 5/2012 | Predick | | 606/250 |
| 2003/0171755 A1 * | 9/2003 | Moseley et al. | | 606/73 |
| 2005/0124994 A1 * | 6/2005 | Berger et al. | | 606/61 |

(Continued)

*Primary Examiner* — Eduardo C Robert
*Assistant Examiner* — Stuart S Bray
(74) *Attorney, Agent, or Firm* — Foley & Lardner LLP (57) ABSTRACT

A laminoplasty rod and rod system that allows for variable angulation, translation (distraction and/or compression) and rotation of a spinal lamina bone portion associated with a laminoplasty. The laminoplasty rod is used with a polyaxial spinal rod bone screw assembly anchored to the vertebra associated with the laminoplasty, and is attachable to the spinal lamina bone portion. The laminoplasty rod system provides positional attachment of the rod to the spinal components and fixation thereof in various orientations. The laminoplasty rod system includes a configured laminoplasty rod that fits into or onto the head of a polyaxial spinal rod bone screw assembly. A bone screw boss, defining a bone screw attachment configuration, is formed at one end of the laminoplasty rod. Preferably, but not necessarily, the bone screw boss is situated at an angled end of the rod having a predefined bend that provides for greater variation in rod orientation.

20 Claims, 5 Drawing Sheets

(56) References Cited

U.S. PATENT DOCUMENTS

| | | |
|---|---|---|
| 2006/0004359 A1* | 1/2006 | Kramer et al. .................. 606/61 |
| 2006/0064092 A1* | 3/2006 | Howland ......................... 606/61 |
| 2006/0229608 A1* | 10/2006 | Foster et al. .................... 606/61 |
| 2006/0241601 A1 | 10/2006 | Trautwein et al. |
| 2007/0118121 A1* | 5/2007 | Purcell et al. ................... 606/61 |
| 2008/0051783 A1* | 2/2008 | Null et al. ....................... 606/61 |
| 2008/0065076 A1* | 3/2008 | Cragg et al. .................... 606/61 |
| 2008/0221622 A1* | 9/2008 | Triplett et al. ................. 606/264 |
| 2008/0312692 A1* | 12/2008 | Brennan et al. ............... 606/246 |
| 2009/0005817 A1* | 1/2009 | Friedrich et al. .............. 606/246 |
| 2009/0222042 A1* | 9/2009 | Firkins et al. ................. 606/246 |
| 2009/0326584 A1* | 12/2009 | Slivka et al. .................. 606/261 |
| 2010/0069960 A1 | 3/2010 | Chaput |
| 2010/0185239 A1 | 7/2010 | Patel et al. |
| 2010/0228291 A1 | 9/2010 | Butler et al. |
| 2010/0318131 A1* | 12/2010 | James et al. .................. 606/264 |
| 2010/0324599 A1* | 12/2010 | Montello et al. .............. 606/264 |
| 2011/0066187 A1* | 3/2011 | Fang et al. .................... 606/254 |
| 2011/0118784 A1* | 5/2011 | Baynham et al. ............. 606/264 |
| 2011/0190822 A1* | 8/2011 | Spitler et al. .................. 606/264 |
| 2011/0245873 A1* | 10/2011 | Winslow et al. .............. 606/254 |

* cited by examiner

LAMINOPLASTY ROD SYSTEM

RELATED APPLICATIONS

This patent application claims the benefit of and/or priority under 35 U.S.C. §119(e) to U.S. Provisional Patent Application Ser. No. 61/257,312 filed Nov. 2, 2009, entitled "Laminoplasty Rod System" the entire contents of which is specifically incorporated herein by this reference.

BACKGROUND OF THE INVENTION

1. Field of the Invention

The present invention relates to procedures and devices for treating problems with the spine and, in particular, to procedures and devices for relieving pressure on the spinal cord.

2. Background Information

The spinal cord and nerve roots in the neck are surrounded and protected by the cervical vertebrae. These bones have an opening called the spinal canal through which the spinal cord passes. Ligaments and blood vessels are also present in the spinal canal. The nerve roots start at the spinal cord and pass through an opening between the vertebrae called the intervertebral foramen (or neural foramen). From there, the nerves extend to other parts of the body. It can thus be appreciated that any compromise to or trouble with the spine can cause various medical problems.

One of these problems is known as spinal stenosis. Spinal stenosis is a condition where there is narrowing of the spinal canal (and often the neural foramen), which causes compression of the spinal cord and/or nerve roots. This narrowing is caused by numerous factors including bone spurs, degeneration of the intervertebral disks and facet joints, and thickening of the ligaments. Among the symptoms spinal stenosis can produce are pain and/or numbness in the arms, clumsiness of the hands, and gait disturbances. The spine may also undergo other compression problems. If left untreated, such problems can lead to a loss in mobility and/or permanent physical damage.

One manner of treating spinal stenosis and other such spinal compression problems is to perform surgery. One prior art surgical procedure is known as a laminectomy. In a laminectomy, pressure against the spinal cord is relieved by removing the spinous process and lamina associated with an affected vertebra. With the posterior portion of the vertebra gone, the spinal cord is thus exposed. Since a laminectomy leaves the spinal cord exposed and removes a substantial portion of the posterior portion of one or more vertebra, various surgical alternatives have been sought.

One such alternative technique or procedure for the decompression of the spine, and especially the cervical spine, is a laminoplasty. In a laminoplasty, the spinal canal is expanded by repositioning the lamina rather than removing it completely, as in a laminectomy. With a laminoplasty, decompression is provided while maintaining the stabilizing effects of the posterior portion of the vertebra through retention of a portion of the posterior portion of the vertebra. The advantage of a laminoplasty is that it increases the size of the spinal canal but leaves a posterior portion that helps keep the spine stable.

In a laminoplasty, one side of a lamina is cut through while the other side of the lamina is grooved to create a "hinged" or "swinging" flap or door of bone. The lamina bone flap is then opened (thereby enlarging the spinal canal) to relieve pressure on the spinal cord. In the typical laminoplasty technique, a wedge or the like is placed between the free side of the lamina and the cut vertebra portion. A plate is then attached to the wedge, the lamina bone flap and the cut vertebra in order to fix the position of the lamina bone flap and the enlarged spinal canal.

The above laminoplasty approach, however, has various drawbacks. For instance, the pre-defined geometry of laminoplasty wedges can create the need for in-situ contouring. Additionally, pre-bent laminoplasty plates and/or other laminoplasty components having pre-defined configurations can add numerous iterations to the installation procedure. As is well known, the longer and more complicated the procedure, the greater the likelihood for problems.

In view of the above, it is apparent that there exists a need for a more versatile laminoplasty implant/implant system.

Additionally, it is apparent that there exists a need for a laminoplasty implant/implant system that provides a better fit with existing anatomies.

Moreover, it is apparent that there exists a need for a laminoplasty implant/implant system that provides for less in-situ contouring and fewer implant iterations.

SUMMARY OF THE INVENTION

The present invention is an improved laminoplasty implant/implant system that provides a better fit with existing anatomies, less in-situ contouring and fewer implant iterations than existing laminoplasty implant/implant systems. Particularly, the present invention is a laminoplasty rod and rod system that allows for variable angulation, translation (distraction and/or compression) and rotation of a spinal lamina bone portion associated with a laminoplasty, prior to fixation thereof.

The laminoplasty rod is configured for use with a polyaxial spinal rod bone screw assembly that is adapted to be anchored to the vertebra associated with the laminoplasty (a lateral mass), and is attachable to the spinal lamina bone portion. The laminoplasty rod system thus provides positional attachment of the laminoplasty rod to the spinal components associated with the laminoplasty and fixation thereof in various orientations.

For attachment to the spinal lamina bone portion, the laminoplasty rod is configured to accept a bone screw. The bone screw attachment configuration allows the bone screw to angulate, thereby accommodating a variety of bone screw orientations relative to the laminoplasty rod and thus into the spinal lamina bone portion.

In one form, the laminoplasty rod system is characterized by a configured laminoplasty rod that fits into or onto the head of a polyaxial spinal rod bone screw assembly. A bone screw boss, defining a bone screw attachment configuration, is formed at one end of the laminoplasty rod. Preferably, but not necessarily, the bone screw boss is situated at an angled end of the rod. The pre-defined bend provides for greater variation in rod orientation.

The laminoplasty rod and rod system is especially, but not necessarily, for a cervical laminoplasty. However, the laminoplasty rod and rod system may be used in other areas of the spine. The laminoplasty rod is made from a biocompatible material such as titanium, stainless steel or the like. Of course, other biocompatible materials may be used.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

An overview of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

Figures 1, 2:
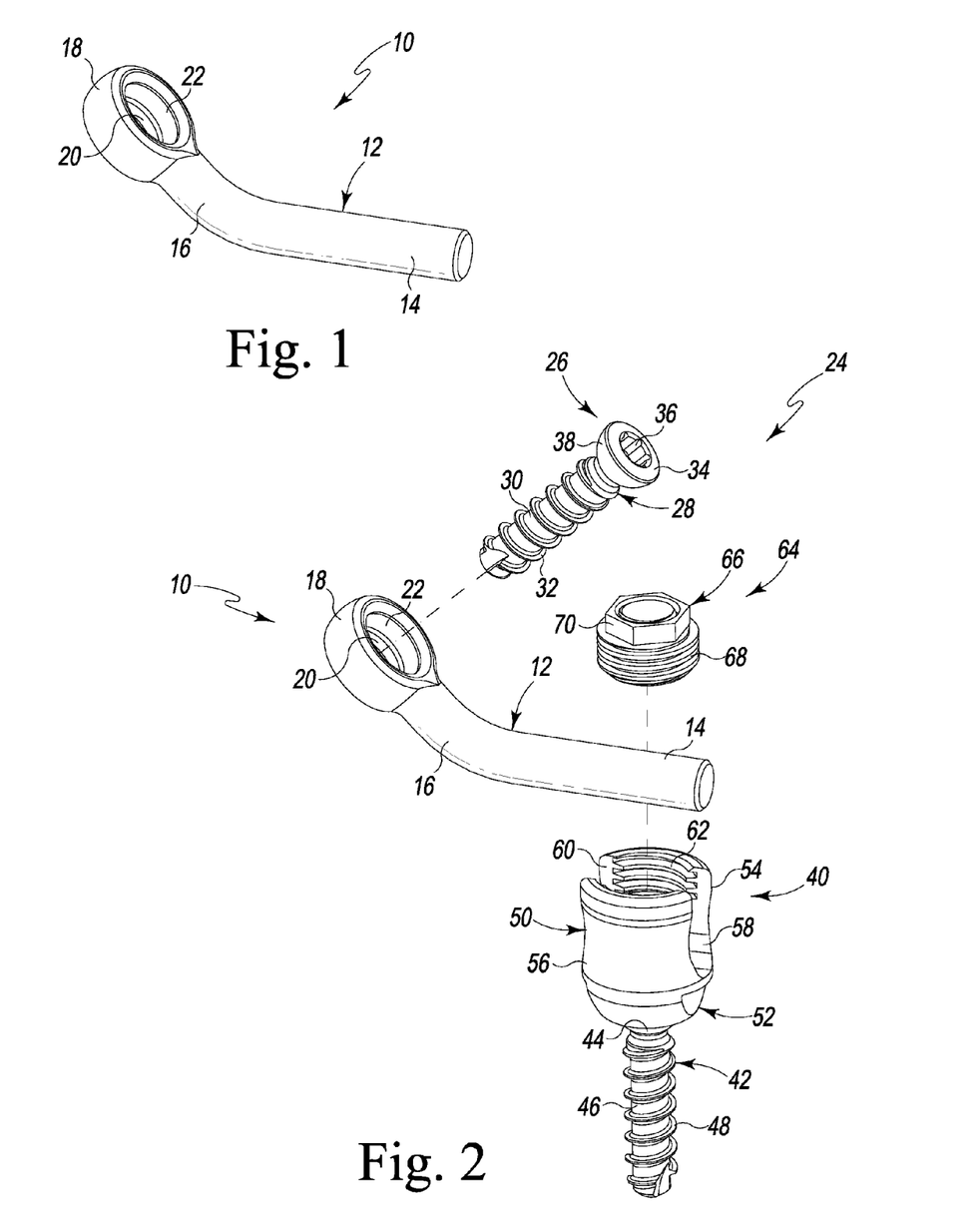
FIG. 1 is a perspective view of a laminoplasty rod fashioned in accordance with the present principles.
FIG. 2 is an exploded perspective view of a laminoplasty rod system utilizing the laminoplasty rod of FIG. 1.

Referring to FIG. 1 there is depicted an exemplary embodiment of a spinal implant fabricated as a laminoplasty rod, generally designated 10, fashioned in accordance with the principles of the present invention. The laminoplasty rod 10 is formed of a biocompatible material such as titanium, stainless steel, or the like. If desired, biocompatible plastics (e.g. PEEK), composites, polymers or the like may be used. The laminoplasty rod 10 is defined by a body 12 having a first rod portion 14, a second rod portion 16 and a bone screw attachment configuration or portion 18, it being understood that the nomenclature first and second is arbitrary.

Figure 3:
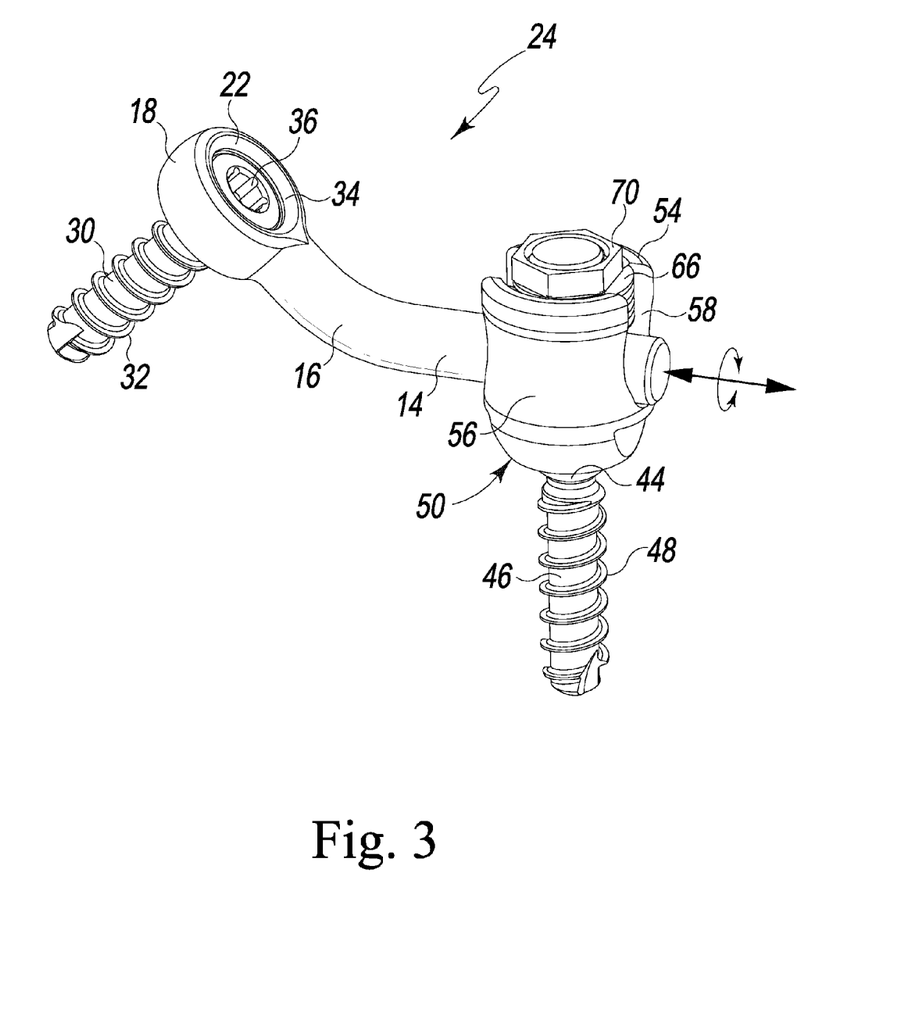
FIG. 3 is an assembled perspective view of the exploded laminoplasty rod system of FIG. 2.
Figure 4:
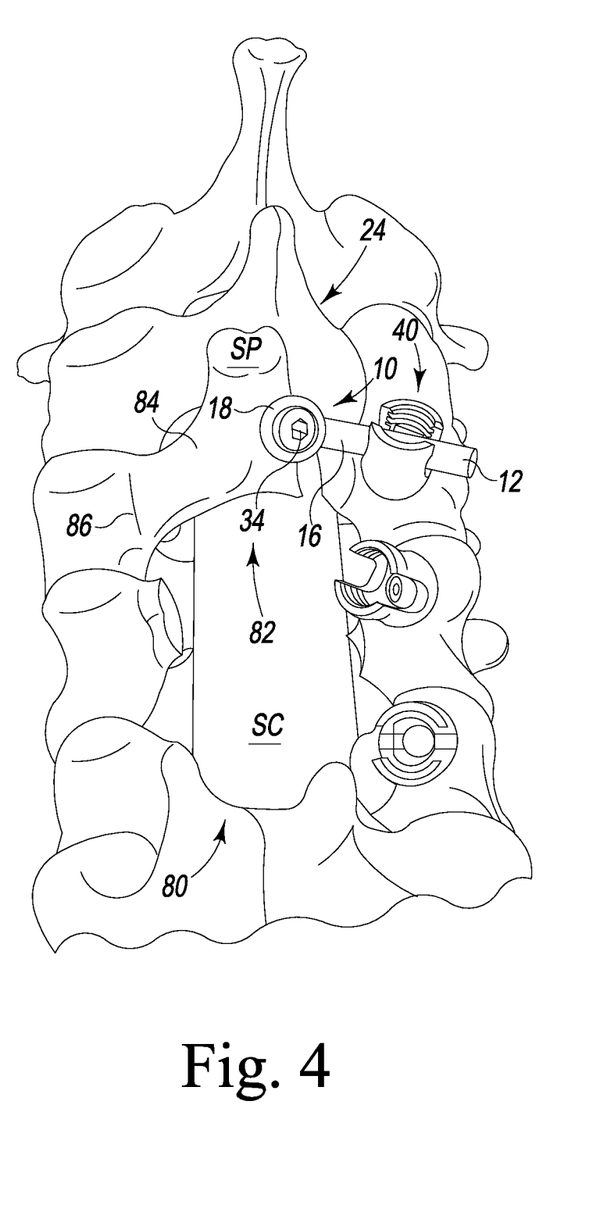
FIG. 4 is posterior perspective view of a portion of a spine with a lower portion thereof having undergone a laminectomy and an upper portion thereof having undergone a laminoplasty utilizing the laminoplasty rod system of FIGS. 2 and 3.

The first rod portion 14 is formed to be received in and attached to a polyaxial spinal rod bone screw assembly such as that depicted in FIGS. 2-4 (i.e. polyaxial spine rod bone screw assembly or spine rod holder assembly 40). Particularly, the first rod portion 14 is configured to be received in slots 58, 60 of a polyaxial head 50 of the spine rod bone screw assembly 40. As such, and in order to provide 360° of rotational positioning and fixation of the body 12 within the head 50, the first rod portion 14 is formed in a generally cylindrical shape having a diameter appropriate for the spine rod bone screw assembly 40 (discussed further below), the cylindrical shape thus defining a generally annular cross-section. Rod portions 14 having cross-sections other than annular are contemplated. The first rod portion 14 has a length appropriate to allow the first rod portion 14 to be received by the head 50, allow lateral (axial) and rotational adjustment of the body 12 while still received in the head 50, and allow variable positioning of the bone screw attachment portion 18 relative to and on the spinal lamina bone portion (see FIG. 4).

The bone screw attachment portion 18 is formed to allow reception of (accept) a bone screw (see, e.g., FIGS. 2-4) in order to attach the laminoplasty rod 10 (and, particularly, the end 18 of the laminoplasty rod 10) to a spinal lamina bone portion (see, e.g., lamina bone portion 84 of FIG. 4). The bone screw attachment portion 18 is formed as a generally annular boss or projection extending from the bend 16 (other shapes or forms are contemplated). As best seen in FIG. 3, the boss 18 has a bore 20 therein that is sized to receive or accept a bone screw 26 (see, e.g. FIG. 2) and, particularly, to allow a threaded shank of a bone screw 26 to pass therethrough while retaining a head 34 of the bone screw 26. In FIG. 1 an upper opening of the bore 20 is shown, it being understood that there is an opposite, lower bore opening that is not seen in the figures. The upper opening of the bore 20 is configured to retain or hold the head 34 of the bone screw 26 (see, e.g. FIG. 2). Particularly, the upper opening begins at a first diameter, then angles or tapers to a second diameter, with the second diameter being smaller than the first diameter. This defines an inwardly and downwardly directed angled or tapered generally annular surface or ledge 22. The ledge 22 retains or holds the head 24 of the bone screw 26 (see, e.g., FIG. 3) while the shank 30 extends through the bore 20.

As best seen in FIG. 2, the head 34 of the body 28 of the bone screw 26 has a generally annular lower angle or taper 38 that extends essentially from the top of the head 34 to the beginning of the shaft 30. The configured head 34 and the ledge 22 of the bore 20 of the boss 18 cooperate to allow the bone screw 26 to swivel relative to the boss 18. This swiveling movement allows the bone screw to be attached to the spinal lamina bone portion 84 (see, FIG. 4) at various angulations or orientations relative to the boss 18.

Referring back to FIG. 1, the second rod portion 16 connects the boss 18 to the first rod portion 14 at an angle relative to the first rod portion 14, the angle being determined by the amount of bend of the second rod portion 16. The angle of the boss 18 determines the angle of the longitudinal (central) axis of the bore 20 and thus the longitudinal axis of a bone screw 26 within the bore 20. The angle of the second rod portion 16 of the laminoplasty rod 10 of FIG. 1 is such that the boss bore axis forms an acute angle with respect to the longitudinal axis of the first rod portion 14. It should be appreciated that laminoplasty rods 10 may be made having various angles (second rod portion 16) if desired to provide a range of laminoplasty rods 10. Therefore, the second rod portion 16 may come in different angles. The laminoplasty rod 10 may be made in various sizes as well.

FIG. 2 depicts an exploded view of an exemplary embodiment of a laminoplasty rod system, generally designated 24, which utilizes the laminoplasty rod 10 of FIG. 1. The laminoplasty implant system 24 consists of the laminoplasty rod 10, the bone screw 26 and the spine rod bone screw assembly 40 including the end cap 64. The laminoplasty rod 10 is receivable in the head 50 of the bone screw assembly 40 with the end cap 64 fixing the first rod portion 14 and thus the laminoplasty rod 10 to the head 50. The boss 18 of the laminoplasty rod 10 receives the bone screw 26 for fixing the laminoplasty rod 10 to the lamina bone portion 84 (see FIG. 4).

The bone screw 26 is characterized by a body 28 having a head 34 and a shaft or shank 30. The shaft 30 has threads or threading 32 as appropriate for a spinal bone screw. The diameter of the threading 32 is sized to allow the shank 30 of the bone screw 26 to pass through the bore 20 of the boss 18. The head 34 includes a socket 36 that is internally configured for mating reception with a screw driving/installation tool or implement (not shown). The underside 38 of the screw head 34 generally extends from the diameter of the screw head to the diameter of the shank 30, providing an annular angle or taper.

The spine rod bone screw assembly 40 is preferably a polyaxial spine rod bone screw assembly or spine rod holder assembly 40 such as is shown. The polyaxial spine rod bone screw assembly 40 consists of a polyaxial spine rod reception head, receptor or head 50 and a polyaxial bone screw 42. The polyaxial spine rod head 50 is defined by a tulip shaped body 52 such as is typical for a polyaxial head. The body 52 defines a first curved side 54 and a second curved side 56 having a first slot 58 defined between first ends of both the first and second sides 54, 56, and a second slot 60 defined between second ends of both the first and second sides 54, 56. The first and second slots 58, 60, disposed diametrically opposite one another, each have a generally rounded end configured to receive the first rod portion 14 of the laminoplasty rod 10 and are disposed diametrically opposite one another. This is shown in FIG. 3. The first side 54 of the body 52 has threads or threading 62 on an inside surface. Likewise, the second side 56 of the body 52 has threads or threading on an inside surface thereof (not seen in the figures). The internal threading of the sides 54, 56 allows threaded receipt of the end cap 64. While not seen, the polyaxial spine rod head 50 has a bore through the bottom thereof for receipt of the polyaxial bone screw 42.

The polyaxial bone screw 42 includes a generally rounded head 44 (of which only a small lower portion can be discerned in the figures) such as is known in the art. The rounded head 44 of the polyaxial bone screw 42 is retained by the body 52 of the polyaxial spine rod head 50 and cooperates with the configured bottom opening to provide polyaxial movement of the polyaxial head 50 about the screw head 44. This allows polyaxial positioning of the polyaxial head relative to the bone screw 42 (and vice versa). The shaft or shank 46 of the polyaxial bone screw 42 extends from the screw head 44 and includes threads or threading 48 thereon.

The end cap 64 is configured to be accepted and retained in and by the polyaxial spine rod head 50 and to fix the axial and rotational position of the laminoplasty rod 10 to and within the polyaxial spine rod head 50 (see FIG. 3). The end cap 64 is defined by a generally cylindrical body 66 having threads or threading 68 on a lower portion thereof. The external threads 68 of the end cap 64 match the internal threading (see threads 62) of the polyaxial spine rod head 50 for threaded receipt of the end cap 64 into the polyaxial spine rod head 50. The end cap 64 has a hexagonal upper portion 70 configured to accept a tool or implement for threading and unthreading (tightening and un-tightening) the end cap 64 into the polyaxial spine rod head 50. Tightening of the end cap 64 compresses the end cap 64 against the first rod portion 14 of the laminoplasty rod 10 or fix the position of the laminoplasty rod 10 into the polyaxial spine rod head 50 (see FIG. 3). This fixation also fixes the angular position of the polyaxial bone screw 42 relative to the polyaxial spine rod head 50.

Reference is now made to FIG. 3 which shows an assembled, but not implanted, laminoplasty rod system 24. The laminoplasty rod 10 is fixed to the bone screw assembly 40 by the end cap 64. The bone screw 26 is shown positioned within the boss 18 of the laminoplasty rod 10. It should be appreciated that the laminoplasty rod 10 may be positioned in and/or relative to the polyaxial spine rod head 50 (/bone screw assembly 40) in various orientations.

Particularly, the laminoplasty rod 10 may be axially positioned along the slots 58, 60 of the polyaxial head 50 as represented by the linear, double headed arrow. Thus, the length from the boss 18 (lamina bone portion connection point) to the polyaxial head 50 (lateral, vertebral mass side connection point) may be adjusted or varied (i.e. shortened or lengthened) as desired to accommodate any physical anatomy and/or other considerations. Additionally, the laminoplasty rod 10 may be rotationally positioned within the slots 58, 60 of the polyaxial head 50 as represented by the annular, double-headed arrow. Thus, the angular orientation of the boss 18, the bore 20 thereof, and thus the bone screw 26 relative to the polyaxial spine rod head 50 (a 'presentment angle' to the lamina bone portion) may be adjusted or varied as desired to accommodate any physical anatomy and/or other considerations. It should also be appreciated that the polyaxial spine rod head 50 may be positioned in various angular orientations relative to a fixation point of its bone screw onto the vertebra. Thus, all of the various angular orientations provide variable angulation, translation (distraction and/or compression) and rotation of the laminoplasty rod 10 and of a spinal lamina bone portion to which it is attached. This provides a quick in-situ positioning of the hinged lamina (spinal lamina bone portion) as easily discerned in FIG. 4.

Referring now to FIG. 4, there is depicted a posterior view of a portion of a cervical area of a human spine, it being understood that such area is exemplary for all those areas of the spine to which the present invention pertains. A section 80 of the spine portion has undergone a laminectomy wherein the spinous processes and lamina of two vertebrae has occurred thus exposing the spinal cord (SC). A section 82, however, has undergone a laminoplasty. One lateral side of the lamina 84 of a vertebra has been removed, while a groove 86 has been carved or etched along the other lateral side of the lamina 84 to provide a hinged lamina bone portion. In this case, the spinous process (SP) of the lamina 84 has not been removed or reduced, as can occur as part of the laminoplasty technique. The present laminoplasty rod system 24 is shown installed with respect to the vertebra/lamina that underwent the laminoplasty.

Regarding the procedural steps of the installation of the present laminoplasty implant system 24 (and not necessarily with respect to the treatment of the lamina), a polyaxial spine rod bone screw assembly 40 is first affixed or attached to the vertebra on the lateral side from which bone was removed from the lamina (i.e. the lateral mass side). The bone screw is allowed to angulate within the boss 18 of the laminoplasty rod 10 for proper affixation of the bone screw and thus the laminoplasty rod 10 to the lamina bone portion 84. Once the laminoplasty rod 10 is secured to the lamina, distraction and/or compression of the lamina can be performed off of the polyaxial screw head of the polyaxial spine rod bone screw system 40 in order to bridge open the lamina and provide an expanded spinal cavity as desired. Once the desired spacing is achieved, the first rod portion 12 of the laminoplasty rod 10 is secured into the polyaxial spine rod head 50 by introducing and then tightening the end cap or set screw 64 (not shown in FIG. 4) to set the polyaxial screw head orientation and laminoplasty rod placement/orientation.

Figure 5:
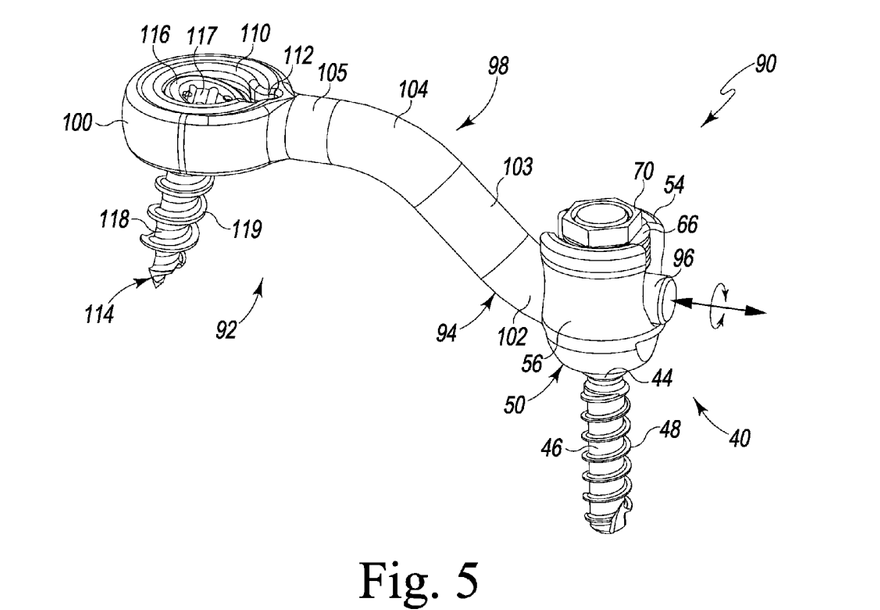
FIG. 5 is a perspective view of another embodiment of the present laminoplasty rod system utilizing another embodiment of a laminoplasty rod fashioned in accordance with the present principles.

Referring to FIG. 5, there is depicted another exemplary embodiment of a laminoplasty implant or rod system, generally designated 90, fashioned in accordance with the present principles. The laminoplasty rod system 90 includes a laminoplasty rod 92, bone screw 114 and spine rod bone screw assembly 40. The spine rod bone screw assembly 40 has been described above with respect to the laminoplasty rod system 24 shown in FIGS. 2 and 3 and is thus incorporated herein by reference. The bone screw 114 is similar to the bone screw 26. As such, the bone screw 114 has a head 116 with a shank 118 extending therefrom. The shank 118 has threads or threading thereon. The head 116 has a socket 11 having a configuration designed to receive a bone screw driver or bone screw installation tool or implement. While not seen, the bone screw 114 has an angled surface between the head 116 and the shank 118 in like manner to the bone screw 26.

Figure 6:
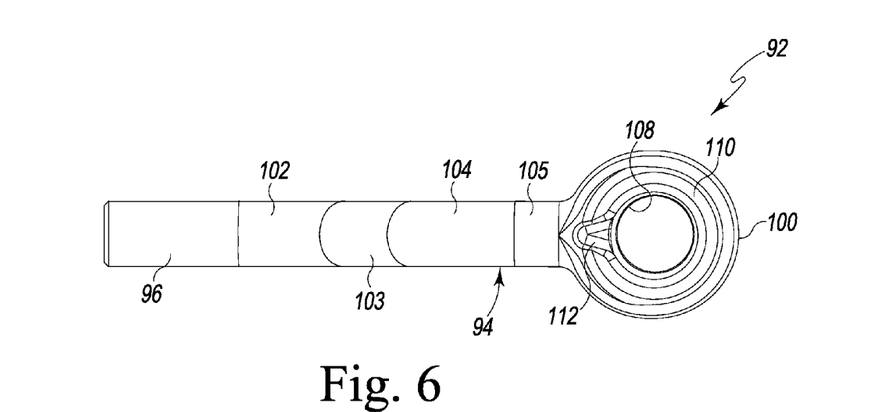
FIG. 6 a top plan view of the laminoplasty rod of the laminoplasty system of FIG. 5.

With additional reference to FIG. 6, the laminoplasty rod 92 has a variation in the contour of its rod portion compared to the laminoplasty rod 10. Particularly, the laminoplasty rod 92 has a double bend or two bends as compared to a single bend (one bend) in the laminoplasty rod 10. Other contours are contemplated. The laminoplasty rod 92 is formed of a biocompatible material such as titanium, stainless steel, or the like. If desired, biocompatible plastics (e.g. PEEK), composites, polymers or the like may be used. The laminoplasty rod 92 is defined by a body 94 having an end rod portion 96, a contoured section 98, and a bone screw attachment configuration, portion or boss 100.

The end rod portion 96 is formed to be received in and attached to the polyaxial spine rod bone screw assembly 40 in like manner to the first rod portion 14 of the laminoplasty rod 10 and as depicted in FIG. 5. Particularly, the end rod portion 96 is configured to be received in slots 58, 60 of the polyaxial spine rod head 50 of the spine rod bone screw assembly 40. As such, and in order to provide 360° of rotational positioning and fixation of the body 94 within the head 50 as represented by the annular, double-headed arrow, the first rod portion 96 is formed in a generally cylindrical shape having a diameter appropriate for the spine rod bone screw assembly 40, the cylindrical shape thus defining a generally annular cross-section. The first rod portion 96 has a length appropriate to allow the first rod portion 96 to be received by the head 50, allow lateral (axial) adjustment of the body 94, as represented by the linear, double-headed arrow, while still received in the head 50, and allow variable positioning of the bone screw attachment portion 100 relative to and on the spinal lamina bone portion.

The contoured portion 98 connects the end rod portion 96 to the bone screw attachment portion 100. Particularly, the contoured portion 98 includes a first bend 102 that angles in a first direction, a transition section 103, and a second bend 104 that angles in a second direction such that the contoured portion 98 defines a double bend. The contoured portion 98 connects to the bone screw attachment portion 100 by a neck or neck portion 105.

The bone screw attachment portion 100 is formed to allow reception of (accept) the bone screw 114 in order to attach the laminoplasty rod 92 (and, particularly, the end 100 of the laminoplasty rod 92) to a spinal lamina bone portion (see, e.g., lamina bone portion 84 of FIG. 4). The bone screw attachment portion 100 is formed as a generally annular boss or projection extending from the neck 105. As best seen in FIG. 6, the boss 100 has a bore 108 therein that is sized to receive or accept the bone screw 114 and, particularly, to allow a threaded shank 118 of the bone screw 114 to pass therethrough while retaining the head 116 of the bone screw 114. An upper opening of the bore 108 is seen in the figures, it being understood that there is an opposite, lower bore opening that is not seen in the figures. The upper opening of the bore 108 is configured to retain or hold the head 116 of the bone screw 114. Particularly, the upper opening begins at a first diameter, then angles or tapers to a second diameter, with the second diameter being smaller than the first diameter. This defines an inwardly and downwardly directed angled or tapered generally annular surface or ledge 110. The ledge 110 retains or holds the head 116 of the bone screw 114 while the shank 118 extends through the bore 108. The bone screw 114 can thus angulate within the boss 100 in like manner to that described above with respect to the laminoplasty rod 10.

The boss 100 has a bone screw back-out prevention mechanism or configuration 112, which may or may not be included on the lamina side of the implant in order to prevent bone screw back-out post surgery. The back-out prevention configuration 112 includes an angled trough or channel that extends into the ledge 110 of the bore 108.

Figure 7:
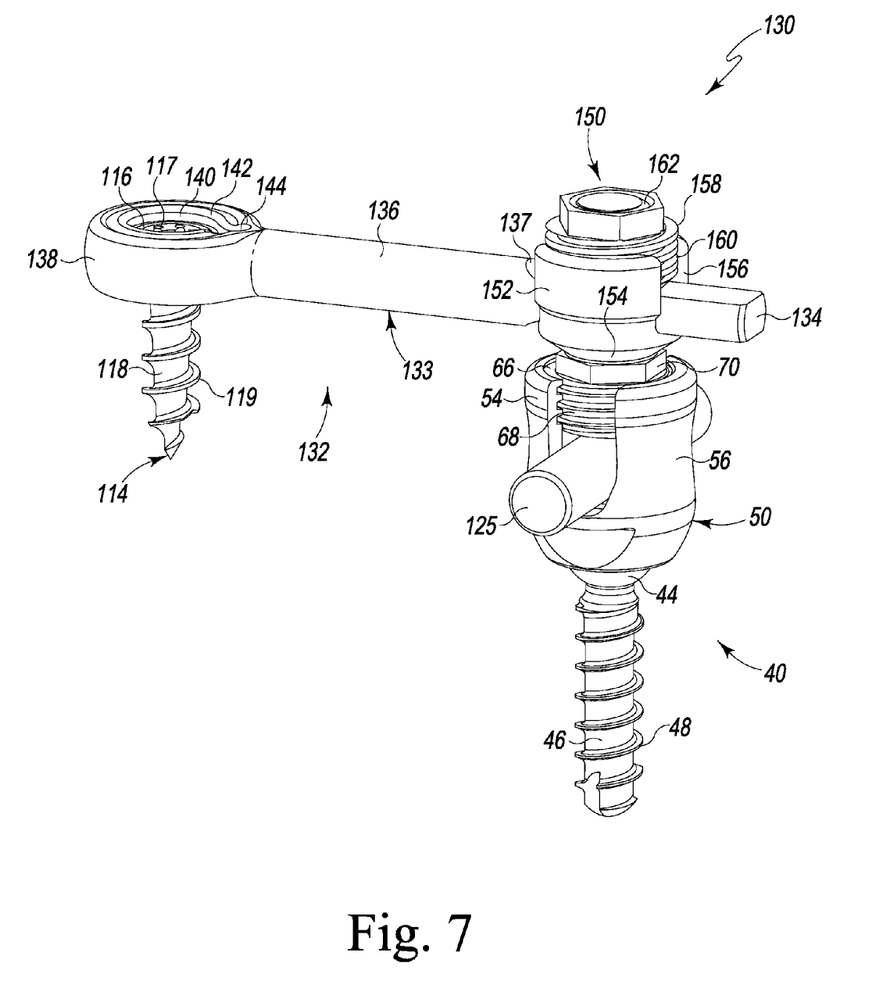
FIG. 7 is a perspective view of a yet another embodiment of the present laminoplasty rod system utilizing yet another embodiment of a laminoplasty rod fashioned in accordance with the present principles.

Referring now to FIG. 7, there is depicted another exemplary embodiment of a laminoplasty implant or rod system, generally designated 130 fashioned in accordance with the present principles. The laminoplasty rod system 130 is configured to be connected to a lateral mass screw and rod holder assembly so that the laminoplasty rod system 130 sits on and above the existing polyaxial screw head rather than within it. This allows the surgeon to also use the lateral mass screw assembly/head in a traditional fusion construct (i.e. screws at several levels connected by a spine rod) and then attach the laminoplasty implant system.

The laminoplasty rod system 130 includes a laminoplasty rod 132, bone screw 114 and spine rod bone screw assembly 40. The spine rod bone screw assembly 40 has been described above with respect to the laminoplasty rod systems 24 and 90 and such discussions are thus incorporated herein by reference. The laminoplasty rod 92 has a variation in the contour thereof compared to the laminoplasty rods 10 and 92, as well as the configuration of its end or first rod portion (i.e. the rod portion that is received in the head 50). Particularly, the laminoplasty rod 132 is straight or generally axial, there being no bends or angles. The laminoplasty rod 132 is formed of a biocompatible material such as titanium, stainless steel, or the like. If desired, biocompatible plastics (e.g. PEEK), composites, polymers or the like may be used. The laminoplasty rod 132 is defined by a body 133 having an end rod section 134, a middle section 136, and a bone screw attachment configuration, portion or boss 138.

The end rod section 134 is formed to be received in and attached to the polyaxial spine rod bone screw assembly 40 in a manner different than for the manner of attachment shown with respect to the laminoplasty rods 10 and 92. It should be appreciated that all of the laminoplasty rods of the present invention may be used in all of the manners of installation and/or use as described herein. Particularly, the end rod section 134 has a generally rectangular (e.g. square) cross section sized to be received in and/or by a laminoplasty screw head extender assembly 150 (extension assembly 150). The extension assembly 150 is configured to be received onto a spine rod bone screw assembly 40 that is already being used to retain a spine rod 125 of a spine rod construct. The extension assembly 150 provides attachment of the laminoplasty rod 132 to the existing spine rod bone screw assembly 40 for a post spine rod installation laminoplasty.

The extension assembly 150 includes an extension head 152 having the general shape of the polyaxial screw head 50 in that the extension head 152 has a generally tulip-shaped configuration. As such, the extension head 152 defines slots 156, 157 (not shown in image) that receive the end rod portion 134. A lower portion 154 of the extension head 152 is configured to have polyaxial rotation with respect to the end cap 161 (different than end cap 66, this piece is same piece as in U.S. provisional patent application Ser. No. 61/139,737, filed Dec. 22, 2008). The end cap 161 has external threads for threaded engagement of the spine rod bone screw assembly 40.

The end rod section 134 has a length appropriate to allow the end rod section 134 to be received by the extension head 152, allow lateral (axial) adjustment of the body 133 while still received in the extension head 152, and allow discrete rotational positioning of the bone screw attachment portion 138 of the laminoplasty rod 132 relative to and on the spinal lamina bone portion.

The middle section 136 connects the end rod section 134 to the bone screw attachment portion 138 at a reduction section 137. The middle section 136 is formed as a generally linear or straight cylinder or rod that is axially connected to the linear end rod section 134 at the reduction section 137. The middle section 136 connects directly to the bone screw attachment portion 138.

The bone screw attachment portion 138 is formed to allow reception of (accept) the bone screw 114 in order to attach the laminoplasty rod 132 (and, particularly, the end 138 of the laminoplasty rod 132) to a spinal lamina bone portion in like manner as the attachment of the laminoplasty rods 10 and 92, described above. The bone screw attachment portion 138 is formed as a generally annular boss or projection extending from the middle section 136. The boss 138 has a bore 140 therein that is sized to receive or accept the bone screw 114 and, particularly, to allow a threaded shank 118 of the bone screw 114 to pass therethrough while retaining the head 116 of the bone screw 114. An upper opening of the bore 140 is seen in the figures, it being understood that there is an opposite, lower bore opening that is not seen in the figures. The upper opening of the bore 140 is configured to retain or hold the head 116 of the bone screw 114. Particularly, the upper opening begins at a first diameter, then angles or tapers to a second diameter, with the second diameter being smaller than the first diameter. This defines an inwardly and downwardly directed angled or tapered generally annular surface or ledge 142. The ledge 142 retains or holds the head 116 of the bone screw 114 while the shank 118 extends through the bore 140. The bone screw 114 can thus angulate within the bore 140 in like manner to that described above with respect to the laminoplasty rods 10 and 92.

The boss 138 has a bone screw back-out prevention mechanism or configuration 144, which may or may not be included on the lamina side of the implant in order to prevent bone screw back-out post surgery, in like manner as the bone screw back-out prevention configuration 112. The back-out prevention configuration 144 includes an angled trough or channel that extends into the ledge 142 of the bore 140.

While the invention has been illustrated and described in detail in the drawings and foregoing description, the same is to be considered as illustrative and not restrictive in character, it being understood that only preferred embodiments and techniques have been shown and described and that all changes and modifications that come within the spirit of the invention are desired to be protected.

What is claimed is:

1. A spinal implant system for attachment to a vertebra and to a spinal lamina bone portion of the vertebra after the vertebra has undergone a laminoplasty, the spinal implant system comprising:
    a first bone screw having a head and a shank;
    a laminoplasty rod having an end rod portion, a bone screw attachment boss, and a contoured portion connecting the end rod portion and the bone screw attachment boss, the end rod portion defining a first axis, the bone screw attachment boss having a bore to receive and engage the bone screw;
    a spinal rod bone screw assembly having a polyaxial head and a second bone screw, the polyaxial head configured to couple to the end rod portion of the laminoplasty rod;
    wherein the contoured portion comprises:
        a first curved portion coupled to the end rod portion;
        a second curved portion coupled to the bone screw attachment boss; and
        a transition portion connecting the first curved portion and the second curved portion and extending at a first angle relative to the first axis of the end rod portion;
    wherein the head of the first bone screw is disposed inside of the bone screw attachment boss;
    wherein the bone attachment screw boss further includes a first point, a second point opposite the bore from the first point, and a linear second axis connecting the first point and the second point, wherein the linear second axis extends at a second angle relative to the transition portion and is parallel and offset relative to the first axis, and wherein the second angle comprises an acute angle, the bone attachment screw boss defines an angled channel extending radially out from the bore into an interior side of the bone screw boss.

2. The spinal implant system of claim 1, wherein the bone screw attachment boss includes a first point, a second point opposite the bore from the first point, and a second axis connecting the first point and the second point, wherein the first axis is parallel and offset from the second axis.

3. The spinal implant system of claim 2, wherein the transition portion extends at a second angle relative to the first axis of the end rod portion, wherein the second angle is an acute angle.

4. The spinal implant system of claim 1, wherein the end portion and the contoured portion are cylindrical, the first rod portion allows 360° rotational positioning thereof relative to the polyaxial head, and the first angle comprises an acute angle.

5. The spinal implant system of claim 4, wherein the bone screw attachment boss includes a back-out prevention mechanism configured to prevent the bone screw from backing out of the bone screw attachment boss.

6. The spinal implant system of claim 1, wherein the first angle comprises an acute angle relative to the first rod portion.

7. The spinal implant system of claim 1, wherein the end rod portion is cylindrical to allow 360° rotational positioning thereof relative to the polyaxial head.

8. A spinal implant for a vertebra having undergone a laminoplasty procedure, the spinal implant comprising:
    a first cylindrical rod defining a first axis and configured for reception in a polyaxial head of a polyaxial vertebral bone screw assembly attached to the vertebra, the first cylindrical rod allowing 360° rotational positioning thereof relative to polyaxial head of a polyaxial vertebral bone screw assembly;
    a second cylindrical rod extending a length and at a first angle relative to the first axis; and
    a bone screw boss at an end of the second rod distal the first rod, the bone screw boss having a bore;
    a bone screw having a head and a shank, the head of the bone screw being in direct engagement with the bone screw boss;
    wherein the bone screw boss further includes a first point, a second point opposite the bore from the first point, and a linear second axis connecting the first point and the second point, wherein the linear second axis extends at a second angle relative to the second cylindrical rod and is parallel and offset relative to the first axis, and wherein the second angle comprises an acute angle the bone screw boss defines an angled channel extending radially out from the bore into an interior side of the bone screw boss.

9. The spinal implant of claim 8, wherein the second angle comprises an acute angle.

10. The spinal implant of claim 9, wherein the first rod, the second rod, and the bone screw boss are formed of PEEK.

11. The spinal implant of claim 8, wherein the first angle comprises an acute angle relative to the first rod portion.

12. The spinal rod of claim 8, wherein the bone screw boss is configured to allow angulation of the vertebral bone screw.

13. A spinal implant assembly for attachment to a vertebra and to a spinal lamina bone portion of the vertebra after the vertebra has undergone a laminoplasty procedure, the spinal implant comprising:
   a first bone screw having a head and a shank;
   a polyaxial vertebral bone screw assembly having a second bone screw and a polyaxial head and a shank;
   a laminoplasty rod comprising:
      a first rod portion defining a first axis and received in the polyaxial head of the polyaxial vertebral bone screw assembly;
      a bone screw boss having a bore to receive the first bone screw;
      a linear transition section located between the first rod portion and the bone screw boss extending a length at a first angle relative to the first axis of the first rod portion and a second angle relative to the bone screw boss; and
   wherein the first bone screw is received in and extends through the bone screw boss such that the head is disposed inside and directly contacts the boss;
   wherein the bone screw boss further includes a first point, a second point opposite the bore from the first point, and a linear second axis connecting the first point and the second point, wherein the linear second axis extends at a second angle relative to the linear transition and is parallel and offset relative to the first axis, and wherein the second angle comprises an acute angle, the bone screw boss defines an angled channel extending radially out from the bore into an interior side of the bone screw boss.

14. The spinal implant of claim 13, wherein the first angle comprises an acute angle relative to the first rod portion.

15. The spinal implant of claim 14, wherein the second angle comprises an acute angle.

16. The spinal implant of claim 13, wherein the first and second rod portions are cylindrical, the first rod portion allows 360° rotational positioning thereof relative to the polyaxial head, and the first angle comprises an acute angle.

17. The spinal implant of claim 16, wherein the second angle comprises an acute angle.

18. The spinal implant of claim 13, further comprising a first curved portion connecting the first rod portion and the linear transition section; and a second curved portion connecting the second rod portion and the linear transition section.

19. The spinal implant of claim 13, wherein the first rod portion defines a first axis and wherein the bone screw boss includes a bore, a first point, a second point opposite the bore from the first point, and a second axis connecting the first point and the second point, wherein the first axis is parallel and offset from the second axis.

20. A method for installing a laminoplasty implant system to a vertebra and to a spinal lamina bone portion of the vertebra after the vertebra has undergone a laminoplasty, the method comprising:
   providing a first bone screw, a laminoplasty rod, and a spinal rod bone screw assembly, the laminoplasty rod having an end rod portion, a bone screw boss, and a contoured portion connecting the end rod portion and the bone screw attachment boss, the contoured portion includes a linear portion defining a first axis, the bone screw boss includes a bone, the spinal rod bone screw assembly having a polyaxial head and a second bone screw, the first bone screw having a head and a shank, wherein the bone screw boss further includes a first point, a second point opposite the bore from the first point, and a linear second axis connecting the first point and the second point, wherein the linear second axis extends at a second angle relative to the linear portion and is parallel and offset relative to the first axis, and wherein the second angle comprises an acute angle, the bone screw boss defines an angled channel extending radially out from the bone screw bore into an interior side of the bone screw boss;
   securing the spinal rod bone screw assembly to the vertebra;
   inserting the first bone screw into the bone screw boss of the laminoplasty rod such that the head is disposed inside and directly contacts the boss, and securing the first bone screw to a lamina bone portion of the vertebra;
   expanding a spinal cavity defined by the vertebra;
   securing the end rod portion of the laminoplasty rod in the head of the spinal rod bone screw assembly.

* * * * *